US011583601B2

(12) United States Patent
Donoshita et al.

(10) Patent No.: US 11,583,601 B2
(45) Date of Patent: Feb. 21, 2023

(54) DRUG-CONTAINING CAPSULE, AND COMPONENT FOR AIR TREATMENT DEVICE

(71) Applicant: DAIKIN INDUSTRIES, LTD., Osaka (JP)

(72) Inventors: Yuka Donoshita, Osaka (JP); Masako Sakamoto, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 127 days.

(21) Appl. No.: 17/003,413

(22) Filed: Aug. 26, 2020

(65) Prior Publication Data

US 2020/0390921 A1    Dec. 17, 2020

Related U.S. Application Data

(63) Continuation of application No. PCT/JP2019/011146, filed on Mar. 18, 2019.

(30) Foreign Application Priority Data

Mar. 29, 2018 (JP) .............................. JP2018-065107

(51) Int. Cl.
*A61L 2/235* (2006.01)
*A01N 25/34* (2006.01)
*F28F 13/18* (2006.01)
*A61K 9/48* (2006.01)
*A61K 9/50* (2006.01)

(52) U.S. Cl.
CPC .............. *A61L 2/235* (2013.01); *A01N 25/34* (2013.01); *A61K 9/4808* (2013.01); *A61K 9/50* (2013.01); *F28F 13/18* (2013.01)

(58) Field of Classification Search
CPC .............................. A61K 9/4808; A61K 9/50
See application file for complete search history.

(56) References Cited

U.S. PATENT DOCUMENTS

| 5,783,561 | A * | 7/1998 | Horwitz ................... A61P 3/00 514/192 |
| 2005/0175748 | A1 * | 8/2005 | Thijssen ................. A01N 25/10 426/326 |
| 2007/0209373 | A1 | 9/2007 | Taira et al. |
| 2010/0122379 | A1 | 5/2010 | Dieckmann et al. |
| 2013/0078308 | A1 | 3/2013 | Hashimoto et al. |
| 2015/0086623 | A1 * | 3/2015 | Chung ................. A61K 9/5084 424/494 |

FOREIGN PATENT DOCUMENTS

| CA | 1319571 C | 6/1993 |
| CA | 2235280 A1 | 4/1997 |
| JP | 54-4282 A | 1/1979 |
| JP | 1-123673 A | 5/1989 |
| JP | 7-173052 A | 7/1995 |
| JP | 11-514360 A | 12/1999 |
| JP | 2002-11340 A | 1/2002 |
| JP | 2005-527633 A | 9/2005 |
| JP | 2005-326137 A | 11/2005 |
| JP | 2007-107806 A | 4/2007 |
| JP | 2011-83222 A | 4/2011 |
| JP | 2013-81929 A | 5/2013 |
| JP | 2016-125698 A | 7/2016 |
| KR | 100707499 B1 * | 4/2005 |
| WO | WO 2015/044673 A1 | 4/2015 |

OTHER PUBLICATIONS

International Preliminary Report on Patentability and English translation of the Written Opinion of the International Searching Authority, dated Oct. 8, 2020, for International Application No. PCT/JP2019/011146.
Extended European Search Report for European Application No. 197/5429.4, dated Oct. 15, 2021.
Jignesh P. et al., "Controlled-release and antibacterial studies of doxycycline-loaded poly(ε-caprolactone) microspheres", Journal of Saudi Chemical Society, vol. 18, No. 5, Nov. 2014, pp. 566-573.
Raffaella et al., "Cotton fabric functionalisation with menthol/PCL micro- and nano-capsules for comfort improvement", Journal of Microencapsulation, vol. 32, No. 7, Oct. 3, 2015, pp. 650-660.
Salima et al., "Antimicrobial activity of Iavandin essential oil formulations against three pathogenic food-borne bacteria", Industrial Crops and Products, vol. 42, Mar. 2013, pp. 243-250.
International Search Report (PCT/ISA/210) issued in PCT/JP2019/011146, dated May 21, 2019.
Written Opinion of the International Searching Authority (PCT/ISA/237) issued in PCT/JP2019/011146, dated May 21, 2019.

* cited by examiner

*Primary Examiner* — Kyle A Purdy
(74) *Attorney, Agent, or Firm* — Birch, Stewart, Kolasch & Birch, LLP

(57) ABSTRACT

A drug-containing capsule (20, 30, 40) includes a capsule material (21, 31, 41) and a drug (22, 32, 42) disposed within the capsule material (21, 31, 41) and having a sterilization action for a specific microorganism. The capsule material (21, 31, 41) includes a degradable part (21a, 31a, 41a) formed of a raw material that is caused to biodegrade by the specific microorganism. This results in suppression of release of the drug while the specific microorganism does not proliferate.

5 Claims, 4 Drawing Sheets

DRUG-CONTAINING CAPSULE, AND COMPONENT FOR AIR TREATMENT DEVICE

TECHNICAL FIELD

The present disclosure relates to a drug-containing capsule and a component for an air treatment device.

BACKGROUND ART

There is a known fin including a base member and a hydrophilic film and used for a heat exchanger (for example, Patent Literature 1). The hydrophilic film includes a plurality of types of drug particles that have a surface covered with a capsule material having controlled dissolubility in water and that are different from each other in the timing of exerting the drug action. In this way, the drug particles can exert the drug action for a long term.

CITATION LIST

Patent Literature

PTL 1: Japanese Unexamined Patent Application Publication No. 2016-125698

SUMMARY

A first embodiment of the present disclosure is directed to a drug-containing capsule (20, 30, 40) including a capsule material (21, 31, 41) and a drug (22, 32, 42) disposed within the capsule material (21, 31, 41) and having a sterilization action for a specific microorganism. The capsule material (21, 31, 41) includes a degradable part (21a, 31a, 41a) formed of a raw material that is caused to biodegrade by the specific microorganism.

DESCRIPTION OF EMBODIMENTS

Figure 1:
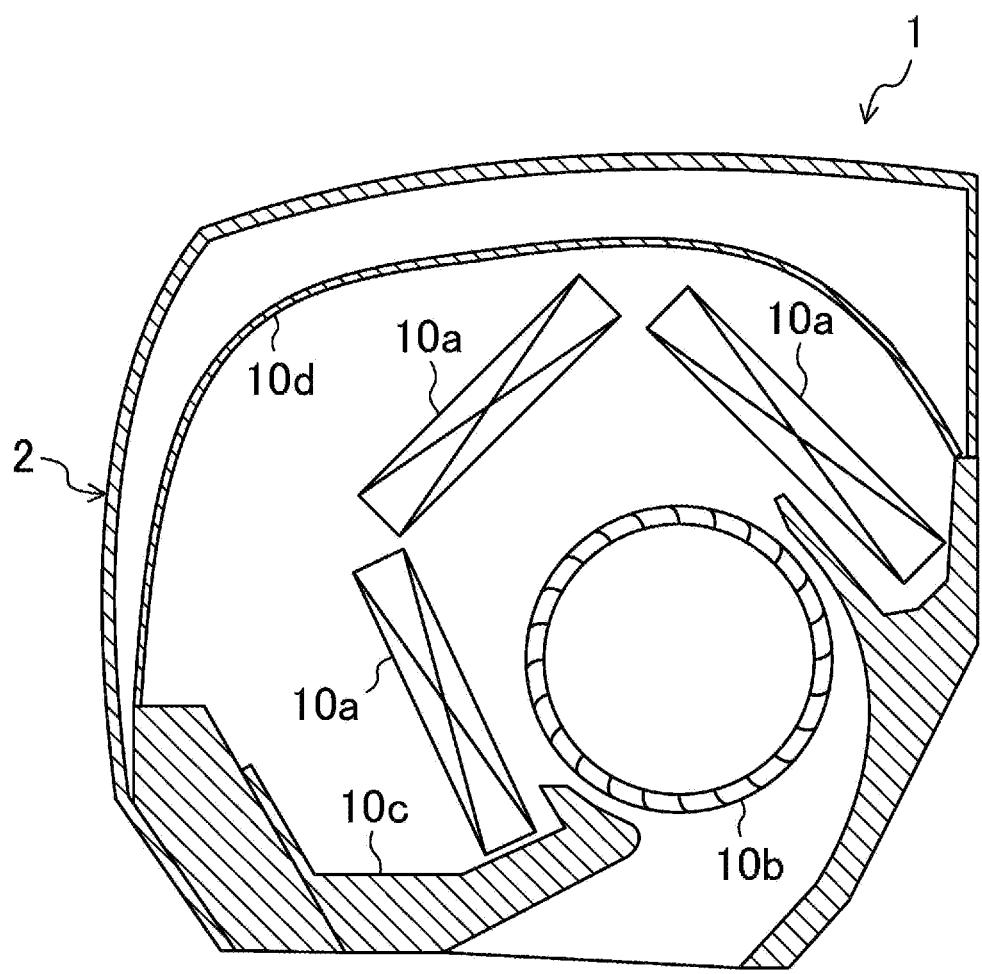
FIG. 1 is a schematic view illustrating the configuration of an air conditioning device according to an embodiment.

A drug-containing capsule (20, 30, 40) according to an embodiment is used for an air treatment device (1). As illustrated in FIG. 1, the air treatment device (1) according to the embodiment is constituted by an air conditioning device (1). This air conditioning device (1) includes a casing (2), a heat exchanger (10a), a fan (10b), a drain pan (10c), a filter (10d), and a flap (not shown) that are each contained in the casing (2), and a duct (not shown). These individually constitute components (10).

Configurations of Near-Surface Regions of Components

Figure 2:
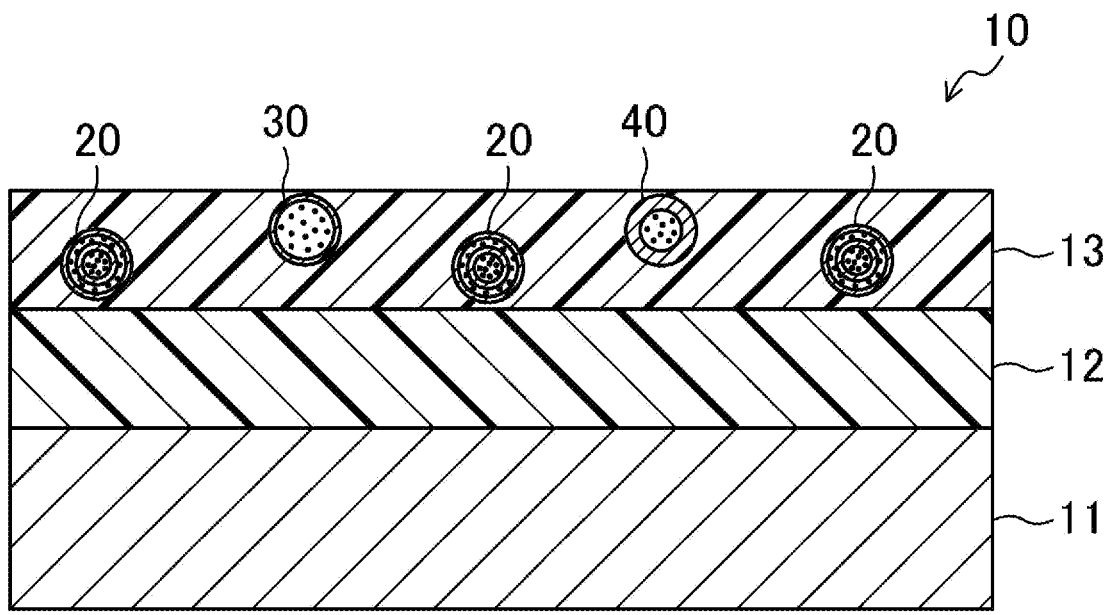
FIG. 2 is a sectional view schematically illustrating a near-surface region of a heat exchanger of an air conditioning device according to an embodiment.

As illustrated in FIG. 2, the components (10) of the air conditioning device (1) each include a base member (11), a corrosion resistant film (12) formed on the base member (11), and a hydrophilic film (13) formed on this corrosion resistant film (12). The base member (11) is formed of, for example, metal or resin. The corrosion resistant film (12) and the hydrophilic film (13) may be formed of, for example, different types of resins. The hydrophilic film (13) constitutes a film.

Drug-Containing Capsule

As illustrated in FIG. 2, the hydrophilic film (13) includes therein a plurality of types of drug-containing capsules (20, 30, 40). In this example, the hydrophilic film (13) includes three types of drug-containing capsules (20, 30, 40), specifically a first drug-containing capsule (20), a second drug-containing capsule (30), and a third drug-containing capsule (40).

Figure 3:
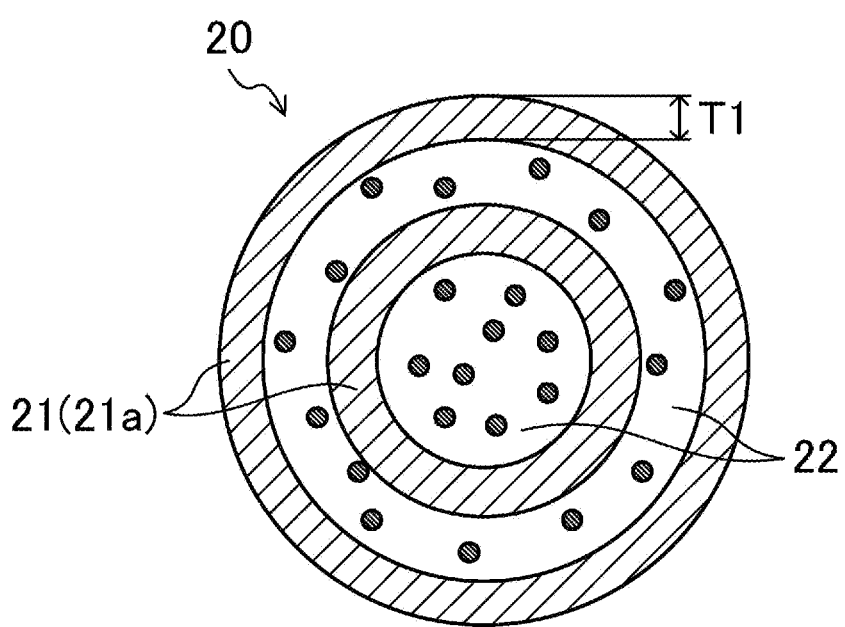
FIG. 3 illustrates an example of a drug-containing capsule according to an embodiment.

As illustrated in FIG. 3, the first drug-containing capsule (20) includes a plurality of (in this example, two) capsule materials (21) disposed as layers and having the shapes of hollow spheres and drugs (22) disposed within the capsule materials (21). The capsule materials (21) include degradable parts (21a) formed of a raw material that is caused to biodegrade by a specific microorganism (specifically, a polymer including caprolactone or a polymer including ethylene adipate). In this example, the capsule materials (21) are wholly constituted by the degradable parts (21a). The drugs (22) have a sterilization action for a specific microorganism and include, for example, a fungicide-bactericide and a plant essential oil. Incidentally, in the drawings, the fungicide-bactericide is illustrated in a white solid color, and the plant essential oil is illustrated as densely hatched areas.

Figure 4:
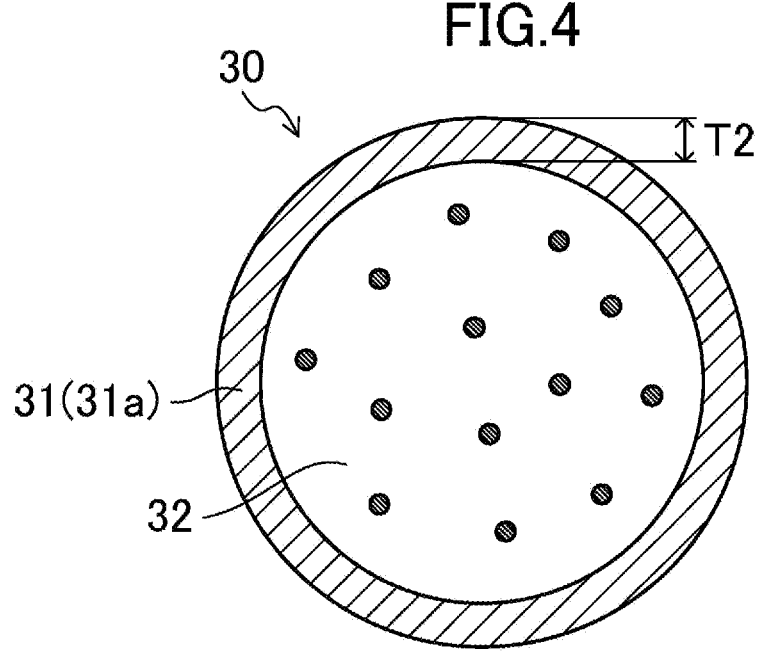
FIG. 4 illustrates an example of a drug-containing capsule according to an embodiment.

As illustrated in FIG. 4, the second drug-containing capsule (30) includes a single capsule material (31) having the shape of, for example, a hollow sphere and a drug (32) disposed within the capsule material (31). The capsule material (31) includes a degradable part (31a) formed of a raw material that is caused to biodegrade by a specific microorganism (specifically, a polymer including caprolactone or a polymer including ethylene adipate). In this example, the capsule material (31) is wholly constituted by the degradable part (31a). The drug (32) has a sterilization action for a specific microorganism and includes, for example, a fungicide-bactericide and a plant essential oil.

Figure 5:
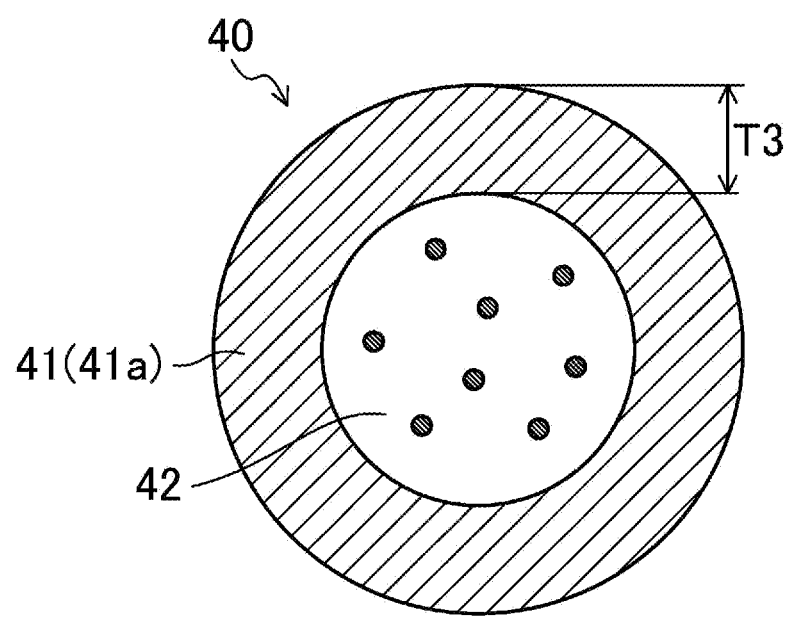
FIG. 5 illustrates an example of a drug-containing capsule according to an embodiment.
Figure 6:
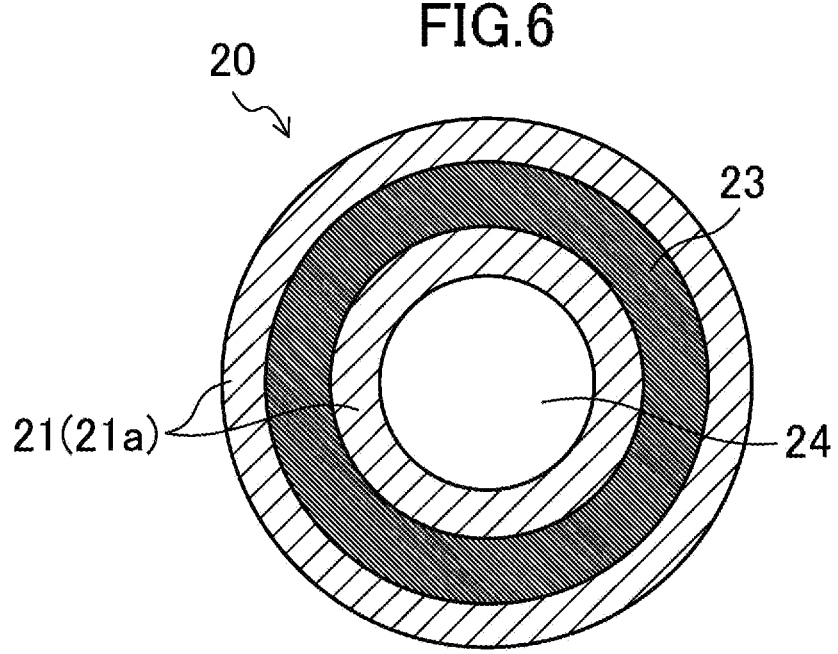
FIG. 6 illustrates an example of a drug-containing capsule according to another embodiment.
Figure 7:
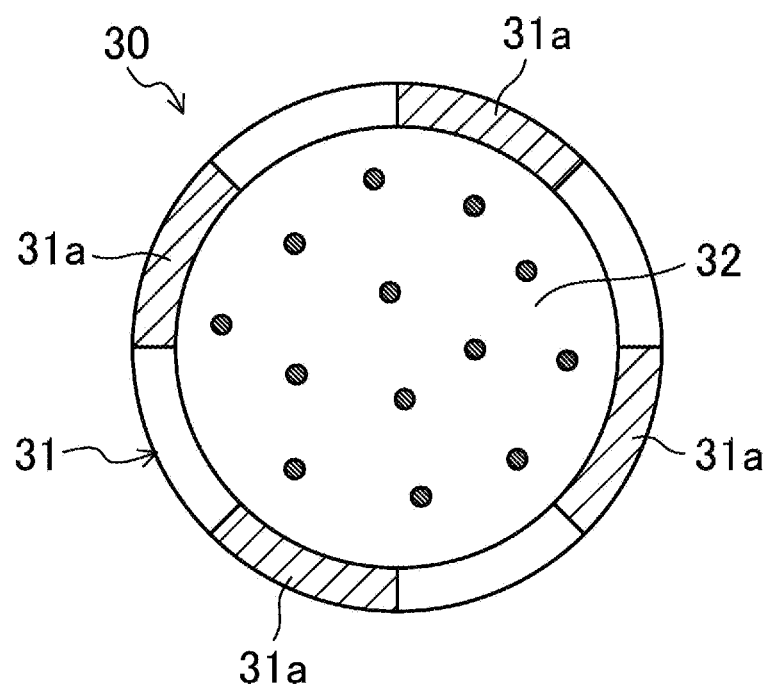
FIG. 7 illustrates an example of a drug-containing capsule according to another embodiment.

As illustrated in FIG. 5, the third drug-containing capsule (40) includes a single capsule material (41) having the shape of, for example, a hollow sphere and a drug (42) disposed within the capsule material (41). The capsule material (41) includes a degradable part (41a) formed of a raw material that is caused to biodegrade by a specific microorganism (specifically, a polymer including caprolactone or a polymer including ethylene adipate). In this example, the capsule material (41) is wholly constituted by the degradable part (41a). The thickness (T3) of the capsule material (41) of the third drug-containing capsule (40) is larger than the thickness (T1) of the outer capsule material (21) of the first drug-containing capsule (20) and the thickness (T2) of the capsule material (31) of the second drug-containing capsule (30) (T1<T3, T2<T3). The drug (42) has a sterilization action for a specific microorganism and includes, for example, a fungicide-bactericide and a plant essential oil.

Incidentally, in this Description, the "specific microorganism" means a microorganism to be destroyed by the drug-containing capsules (20, 30, 40). The microorganism is specifically a mold, a yeast, or a bacterium proliferating in the air treatment device (1): the mold includes at least one of *Penicillium* molds, *Cladosporium* molds, *Aspergillus* molds, *Toxicocladosporium* molds, *Engyodontium* molds, *Aureobasidium* molds, *Alternaria* molds, *Paecilomyces* molds, *Tricoderma* molds, *Nigrospora* molds, *Chaetomium* molds, *Ulocladium* molds, *Fusarium* molds, *Eurotium* molds, *Curvularia* molds, *Rhodotorula* molds, *Chaetomium* molds, *Mucor* molds, and *Rhizopus* molds; the yeast includes at least one of true fungi that are collectively called yeast; and the bacterium includes at least one of Arthrobacter bacteria, *Baccilus* bacteria, *Serratia* bacteria, and *Staphylococcus aureus*.

Exertion of Drug Action

Hereinafter, how the drug-containing capsules (20, 30, 40) exert the drug action will be described.

For example, on the surface of the heat exchanger (10a) of the air conditioning device (1), moisture in the air condenses during a cooling operation to generate drain water, which leads to proliferation of a specific microorganism.

The proliferating specific microorganism causes biodegradation of the capsule materials (21, 31, 41) of the first to third drug-containing capsules (20, 30, 40). In this case, first, the outer capsule material (21) of the first drug-containing capsule (20) and the capsule material (31) of the second drug-containing capsule (30) are perforated. This causes release of the drugs (22, 32) from within the capsule materials (21, 31) to destroy the specific microorganism.

When the specific microorganism further proliferates, the inner capsule material (21) of the first drug-containing capsule (20) is then perforated. This causes release of the drug (22) from within the capsule material (21) to destroy the specific microorganism.

When the specific microorganism further proliferates, the capsule material (41) of the third drug-containing capsule (40) is then perforated. This causes release of the drug (42) from within the capsule material (41) to destroy the specific microorganism.

In this way, the first to third drug-containing capsules (20, 30, 40) exert the drug action at the spot and timing of the proliferation of the specific microorganism. The capsule materials (21, 31, 41) are perforated at timings different from each other, so that the drug action is exerted for a relatively long term.

Advantages of Embodiments

The drug-containing capsules (20, 30, 40) according to these embodiments include capsule materials (21, 31, 41) and drugs (22, 32, 42) disposed within the capsule materials (21, 31, 41) and having a sterilization action for a specific microorganism, wherein the capsule materials (21, 31, 41) include degradable parts (21a, 31a, 41a) formed of a raw material that is caused to biodegrade by the specific microorganism.

The inventors of the present application focused on disposition of drug-containing capsules (20, 30, 40) for a specific microorganism at the spot of proliferation of the specific microorganism. They have found that, by using a raw material that is caused to biodegrade by the specific microorganism to form at least portions of the capsule materials (21, 31, 41), the specific microorganism is destroyed at the spot and timing of proliferation. The degradable parts (21a, 31a, 41a) of the capsule materials (21, 31, 41) of the embodiments are caused to biodegrade by a specific microorganism at the spot of proliferation of the microorganism. This causes release of the drugs (22, 32, 42) from within the capsule materials (21, 31, 41) to destroy the proliferating microorganism. In this way, the drug action of the drugs (22, 32, 42) is exerted at the spot and timing of proliferation of the specific microorganism.

The specific microorganism is a mold, a yeast, or a bacterium proliferating in the air treatment device (1). Therefore, the embodiments provide drug-containing capsules (20, 30, 40) that effectively act against the mold, the yeast, or the bacterium proliferating in the air treatment device (1).

The mold includes at least one of *Penicillium* molds, *Cladosporium* molds, *Aspergillus* molds, *Toxicocladosporium* molds, *Engyodontium* molds, *Aureobasidium* molds, *Alternaria* molds, *Paecilomyces* molds, *Tricoderma* molds, *Nigrospora* molds, *Chaetomium* molds, *Ulocladium* molds, *Fusarium* molds, *Eurotium* molds, *Curvularia* molds, *Rhodotorula* molds, *Chaetomium* molds, *Mucor* molds, and *Rhizopus* molds; the yeast includes at least one of true fungi that are collectively called yeast; and the bacterium includes at least one of Arthrobacter bacteria, *Baccilus* bacteria, *Serratia* bacteria, and *Staphylococcus aureus*. The inventors of the present application have newly found that such molds, yeasts, or bacteria proliferate in the air treatment device (1). In the embodiments, a raw material that is caused to biodegrade by such a mold, a yeast, or a bacterium is used to form capsule materials (21, 31, 41). Therefore, the embodiments provide drug-containing capsules (20, 30, 40) that effectively act against such a specific mold, yeast, or bacterium.

In the drug-containing capsules (20, 30, 40) according to the embodiments, the raw material that is caused to biodegrade by such a specific microorganism is a polymer including caprolactone or a polymer including ethylene adipate. Therefore, the embodiments provide drug-containing capsules (20, 30, 40) that effectively act against the microorganism that causes biodegradation of such a polymer.

In the first drug-containing capsule (20) according to the embodiment, the capsule material (21) includes two capsule materials (21) disposed as layers, and the drug (22) is disposed within each of the capsule materials (21). Thus, upon biodegradation of the outer capsule material (21), the drug (22) disposed therein is released to destroy the specific microorganism. Subsequently, upon biodegradation of the inner capsule material (21), the drug (22) disposed therein is released to destroy the specific microorganism. In this way, such first drug-containing capsules (20) each provide a drug action twice.

The component (10) for the air treatment device (1) according to the embodiment includes the film (13) including the drug-containing capsules (20, 30, 40). Thus, the embodiment, in the air treatment device (1), effectively suppresses proliferation of the specific microorganism on the component (10) including the film (13) including the drug-containing capsules (20, 30, 40).

In the component (10) for the air treatment device (1) according to the embodiment, the film (13) includes the first to third drug-containing capsules (20, 30, 40), and, in the third drug-containing capsule (40), the thickness (T3) of the degradable part (41a) of the capsule material (41) is larger than the thicknesses (T1, T2) of the degradable parts (21a, 31a) of the capsule materials (21, 31) of the first and second drug-containing capsules (20, 30). Thus, compared with the first drug-containing capsule (20) and the second drug-containing capsule (30), in the third drug-containing capsule (40), perforation of the capsule material (21, 31, 41) due to biodegradation occurs at a later timing, so that the drug action is exerted in a later period. Therefore, compared with a case where the thicknesses (T1 to T3) of the capsule materials (21, 31, 41) of all the drug-containing capsules (20, 30, 40) are substantially the same, the total period of exerting the drug action by the first to third drug-containing capsules (20, 30, 40) becomes longer.

The drug-containing capsule (20, 30, 40) according to the embodiment includes the capsule material (21, 31, 41) including the degradable part (21a, 31a, 41a) formed of a polymer including caprolactone or a polymer including ethylene adipate, and the drug (22, 32, 42) disposed within the capsule material (21, 31, 41) and having a sterilization action for a microorganism. Thus, the degradable part (21a, 31a, 41a) of the capsule material (21, 31, 41) is caused to biodegrade by a microorganism proliferating in the air treatment device (1). This causes release of the drug (22, 32, 42) from within the capsule material (21, 31, 41) to destroy the microorganism. In this way, in the air treatment device (1), the drug action of the drugs (22, 32, 42) is exerted at the spot and timing of proliferation of the microorganism.

Other Embodiments

The above-described embodiments may be provided so as to have the following configurations.

In the above-described embodiment, the air treatment device (1) is constituted by the air conditioning device (1). Alternatively, the air treatment device (1) may be constituted by, for example, an air purification device, a humidity control device, or a ventilation device. In this case, the component (10) may be constituted by, for example, a fan or filter of the air purification device, a humidifying unit, fan, or filter of the humidity control device, or a fan, filter, or duct of the ventilation device.

In the above-described embodiment, the drugs (22) disposed within the two capsule materials (21) of the first drug-containing capsule (20) are of the same type. Alternatively, as illustrated in FIG. 6, the type of a drug (23) disposed within the outer capsule material (21) and the type of a drug (24) disposed within the inner capsule material (21) may be different from each other. Incidentally, in this example, the drug (23) disposed within the outer capsule material (21) is a fungicide-bactericide, while the drug (24) disposed within the inner capsule material (21) is a plant essential oil. The number of the capsule materials (21) of the first drug-containing capsule (20) may be three or more.

In the above-described embodiment, the capsule materials (21, 31, 41) of the first to third drug-containing capsules (20, 30, 40) are wholly constituted by the degradable parts (21*a*, 31*a*, 41*a*). Alternatively, as illustrated in FIG. 7, for example, in the second drug-containing capsule (30), only portions of the capsule material (31) may be constituted by the degradable parts (31*a*). In this case, the degradable parts (31*a*) are caused to biodegrade by a specific microorganism to release the drug (32). The same applies to the first and third drug-containing capsules (20, 40).

The drug-containing capsules (20, 30, 40) included in the hydrophilic film (13) may be of two or less types, or four or more types.

The embodiments and modifications have been described so far, and it would be understood that the forms and details can be changed in various ways without departing from the spirit and scope of the Claims. The above-described embodiments and modifications can be appropriately combined or substituted unless the function of the subject matter of the present disclosure is degraded. industrial applicability As has been described so far, the present disclosure is useful for drug-containing capsules and components for air treatment devices.

EXPLANATION OF REFERENCES

1 air conditioning device (air treatment device)
10 component
10*a* heat exchanger (component)
10*b* fan (component)
10*c* drain pan (component)
10*d* filter (component)
13 hydrophilic film (film)
20 first drug-containing capsule (drug-containing capsule)
21 capsule material
21*a* degradable part
22 drug
30 second drug-containing capsule (drug-containing capsule)
31 capsule material
31*a* degradable part
32 drug
40 third drug-containing capsule (drug-containing capsule)
41 capsule material
41*a* degradable part
42 drug
T1 to T3 thicknesses (of degradable parts)

The invention claimed is:

1. An air treatment device having an interior portion that includes an antimicrobial film wherein:

the air treatment device has an outer casing that encloses an interior portion that includes components comprising at least a fan, a heat exchanger and a filter, wherein the interior portion and components have a surface of metal or a resin, a corrosion resistant layer comprising a resin, the resin being disposed on one or more of the interior portion or component surfaces; and an antimicrobial film wherein the antimicrobial film is disposed on the corrosion resistant layer and the antimicrobial film comprises a hydrophilic layer comprising a resin, wherein the wherein the hydrophilic layer contains antimicrobial capsules that comprise, an outer layer capsule material of one or more layers of caprolactone or a polymer including ethylene adipate, wherein the capsule material that degrades upon exposure to certain microorganisms, and an active material disposed within the outer layer capsule material, wherein the active material comprises at least one of a fungicide, bactericide or plant essential oil that kills the microorganisms.

2. The air treatment device according to claim 1, wherein the microorganism is a mold, a yeast, or a bacterium proliferating in the air treatment device.

3. The air treatment device according to claim 2, wherein the mold includes at least one of *Penicillium* molds, *Cladosporium* molds, *Aspergillus* molds, *Toxicocladosporium* molds, *Engyodontium* molds, *Aureobasidium* molds, *Alternaria* molds, *Paecilomyces* molds, *Tricoderma* molds, *Nigrospora* molds, *Chaetomium* molds, *Ulocladium* molds, *Fusarium* molds,

*Eurotium* molds, *Curvularia* molds, *Rhodotorula* molds, *Chaetomium* molds, *Mucor* molds, and *Rhizopus* molds, the yeast includes at least one of true fungi that are collectively called yeast, and the bacterium includes at least one of Arthrobacter bacteria, *Baccilus* bacteria, *Serratia* bacteria, and *Staphylococcus aureus*.

4. The air treatment device according to claim 1, wherein the capsule material comprises a plurality of encapsulating layers, and the active material is disposed within each of the encapsulating layers.

5. The air treatment device according to claim 1, wherein the hydrophilic layer of the film contains a plurality of different types of the antimicrobial capsules having capsule material layers that differ with respect to thickness from other antimicrobial capsules.

\* \* \* \* \*